United States Patent [19]

Ehrly et al.

[11] 4,201,470

[45] May 6, 1980

[54] METHOD AND APPARATUS FOR MEASUREMENT AND REGISTRATION OF THE AGGREGATION RATE OF PARTICLES SUSPENDED IN A LIQUID

[76] Inventors: Albrecht Ehrly, Am Kellersbusch 10, 6072 Dreieich; Hans J. Schmitt, Rimbacherstrasse 27, 6149 Grasellenbach, both of Fed. Rep. of Germany

[21] Appl. No.: 879,630

[22] Filed: Feb. 21, 1978

[30] Foreign Application Priority Data

Feb. 24, 1977 [DE] Fed. Rep. of Germany ....... 2707962
Jan. 18, 1978 [DE] Fed. Rep. of Germany ....... 2802033

[51] Int. Cl.² ........................................... G01N 33/16
[52] U.S. Cl. ..................................... 356/39; 73/64.1; 356/427
[58] Field of Search ................... 356/39, 40, 246, 427; 73/64.1; 128/2 G

[56] References Cited

U.S. PATENT DOCUMENTS

| | | | |
|---|---|---|---|
| 3,263,554 | 8/1966 | Pickels | 356/246 |
| 3,650,698 | 3/1972 | Adler | 356/39 |
| 3,819,271 | 6/1974 | Beug et al. | 356/39 |
| 4,066,360 | 1/1978 | Breddin et al. | 356/39 |
| 4,116,564 | 9/1978 | Renaud et al. | 73/64.1 X |

*Primary Examiner*—Vincent P. McGraw
*Attorney, Agent, or Firm*—Steinberg & Blake

[57] ABSTRACT

A method for the measurement of the aggregation rate of particles suspended in a liquid, particularly of red blood corpuscles in the blood by measuring the intensity of a light beam impinging on the blood sample and leaving the sample again, wherein said blood sample is arranged in a disc cuvette in the horizontal beam path of a light source and is subjected to a shear movement during the course of the measurement of the light beam leaving the sample, and an apparatus for carrying out this measurement.

32 Claims, 10 Drawing Figures

METHOD AND APPARATUS FOR MEASUREMENT AND REGISTRATION OF THE AGGREGATION RATE OF PARTICLES SUSPENDED IN A LIQUID

The invention relates to a method for the measurement and, if necessary, for the registration of the aggregation rate of particles suspended in a liquid and relates furtheron to the apparatus for performing the method of the invention.

The invention is particularly directed to the measurement of the aggregation rate of red blood corpuscles in the blood as a function of the time and relates to a method for obtaining measuring values corresponding to the blood sedimentation rate after Westergren.

The invention relates furtheron to an apparatus for performing this method.

In the overwhelming majority of organic disorders, the aggregation of the red blood corpuscles (erythrocyte aggregation) in the blood is the stronger, the more serious the disorder is. As the erythrocyte aggregates will in view of Stoke's sedimentation law sediment more rapidly than individual non-aggregated particles, in addition to the aggregation of the erythrocytes (red blood corpuscles) sedimentation of the aggregates will occur. The sedimentation rate of the erythrocyte aggregates is predominantly determined by two factors:

(a) by the kind and the concentration of the aggregate-sponsoring proteines, and (b) by the number of the suspended erythrocytes per volume of plasma (compare Ehrly, A. M. and Fink, M. M.: Blutkoerperchensenkungsgeschwindigkeit bei verschiedenen Haematokritwerten. Med. Welt vol 22, 1960 (1971).

The higher the concentration of the aggregate sponsoring substances and the smaller the number of the suspended erythrocytes in the blood, the higher the sedimentation rate, which in practice is measured in the form of the blood corpuscle sedimentation rate after Westergren.

Determination of the blood corpuscle sedimentation rate is accomplished as a universal search method for organically pathologic processes (such as rheumatism, tuberculosis, cancer, inflammations) and constitutes one of the most frequently employed laboratory methods in medicine. In the execution of this determination of the blood corpuscle sedimentation rate, about 4 milliliters of venous blood are mixed with about 1 milliliter of an anticoagulant sodium citrate solution and is then drawn up into a particular burette having a length of 200 mm and an overall width of about 2 mm and is placed in an upright position. After one and two hours each, phase separation is observed and the erythrocyte-free plasma column is read off and is indicated in the form of the millimeter per hour value.

This determination method of the blood corpuscle sedimentation rate is rather time consuming and numerous attempts have been made to improve this determination method and to replace it against a more rapid process.

It has been tried to this end to abbreviate the procedure by oblique sedimentation, centrifugation, heating or the like. The results obtained however were far from being satisfactory as they were not comparable to the results of the hitherto-used Westergren blood sedimentation rate method, and that is why these modified methods were not accepted in clinical practice.

Light-optical methods have furtheron been used in order to determine the aggregation tendency or the aggregation rate, respectively. For this purpose, the vertical illumination method, or reflectometry, respectively, is employed, on one hand, and the transmission method is used on the other wherein the increase of the light penetrating through a thin blood layer is determined.

Zijlstra has studied reflectometry extensively and has described this method in the article "Syllektometrie" in the book "Oximetrie, Theorie und klinische Anwendung" by Kurt Kramer 1960. In accordance with his method, the variation of the reflected light is employed as a measure for the coaggregation of the erythrocytes.

From German Offenlegungsschrift No. 2,413,285, a transmission method has furtheron been known, wherein a blood sample is arranged in a mixing chamber made of transparent material and is made to rotate with the aid of a cone-shaped body of transparent material extending into the sample. The transmission of a light beam passed vertically through the cone-shaped rotation body and the blood sample is determined by means of a photometer and is graphically plotted versus time. This method uses very small amounts of blood; the aggregation is measured under flow stand still. Under these process conditions however sedimentation and disintegration effects cannot be excluded. The formation of larger aggregates from the individual erythrocytes is furtheron not possible in view of the tight chamber slit of only a few microns, and the shear forces appearing in a cylindric tube during the course of the blood sedimentation are furthermore not taken into consideration when measuring under flow stand still so that values comparable to the normal blood sedimentation rate cannot be obtained by means of this prior art method.

Based on extensive tests, Applicants have found out that in light-optical methods sedimentation of the blood constitutes an essential source of errors and that therefore measurements in the stationary state of the blood sample bear a lot of mistakes.

Based on earlier researches and on the tests performed by Applicants, it has been found that the erythrocytes contained in the blood, coagglomerate in the beginning to form simple coin roll shaped primary aggregates which, on their part, combine to form greater-volume secondary aggregates. It has been found that this aggregation of the particles is particularly favored by extremely small shear forces which have to be taken to be present also in the so-called Westergren tubes.

Factual sedimentation of the erythrocytes which in the measurement of the blood corpuscle sedimentation rate serves as the measure for the aggregation tendency of the red blood corpuscles must in case of a light-electric method for obtaining a value comparable to that obtained by a common blood sedimentation be avoided considering that disintegration effects lead to disturbances of the light transmission and of the reflection. It has furtheron shown that for a light-optical measuring method the spatial conditions in the sample body must be so that the large secondary aggregates can form without hindrance.

Particularly in case of blood samples of patients suffering from tumors or anaemia where the sedimentation rate is particularly increased and the disintegration between blood and plasma starts already within the first minute, special attention must be paid to avoid such sedimentation during the course of the measuring process in order to obtain unobjectionable values comparable to those obtained by the hitherto-common blood sedimentation rate.

It was therefore the aim of the present invention to provide a new method for the measurement and, if necessary, the registration of the aggregation rate of particles suspended in a liquid, particularly of the red blood corpuscles in the human blood, wherein sedimentation of the blood and the sources of error connected therewith are substantially excluded and by which the blood sample is offered optimum conditions for the coagglomeration of the particles contained in the liquid so that a favorable contact quota (impact quota) of the particles is obtained while however no sedimentation and thus coarse disintegration of the blood samples is experienced. The measuring time of the method of the invention should be short and measurements of extremely small sample amounts should be possible which yield results comparable to the sedimentation rate values after Westergren. It is furtheron the aim of the present invention to provide an apparatus for performing the method of the invention.

The problem of the invention is solved with the aid of a method of the kind described in the beginning by measuring the intensity variation of a light beam impinging on the blood sample and leaving it again, which is characterized in that the blood sample is arranged within a disc cuvette (optical cell) in the horizontal beam path of a light source and is subjected, during the course of the measurement of the light beam leaving the sample, to a shear movement. Such a thorough mixing avoids the sedimentation of the particles which has been recognized to be very disadvantageous for the light-optical method, through which an essential error of the prior art measuring methods is excluded.

Based on extensive tests, Applicants have furtheron found out that the reproducibility of the above mentioned method for measuring the aggregation rate of the red blood corpuscles in the blood may substantially be improved by measuring the intensity variation as a function of time of a light beam impinging on the blood sample and leaving the sample again if prior to the factual measuring process the blood sample in the disc cuvette is thoroughly mixed so that all the reversible erythrocyte aggregates are dispersed. In the course of the subsequent slow rotation, the blood is subjected to a little, for aggregation however favorable, shear movement (mixture). From the start of the slow shear movement, which avoids sedimentation, the measuring process so goes on that the amount of light leaving the sample is measured during rotation of the cuvette in the horizontal path of a light source.

It has particularly turned out that by the feature of the invention of the thorough mixing at the beginning of the measurement, substantially better starting situations for the measurement are obtained and optimum conditions are provided which essentially correspond to the measuring conditions in case of the blood corpuscle sedimentation rate after Westergren through shaking and tilting of the blood sample prior to the drawing into the sedimentation tube.

The shear movement produced within the blood sample favors the erythrocyte aggregation by increasing the impact possibilities while at the same time deposition or sedimentation, respectively, is avoided.

It has shown that the measurement can be performed as a transmission measurement as well as a reflection measurement.

This means that on one hand the intensity variation of the light beam penetrating through the blood sample can be measured while on the other hand the intensity variation of the light beam reflected from the blood sample can be measured, too, the angle of impact relative to the cell plane being preferably 45°.

In order to eliminate temperature effects in the course of the measurement the blood sample may be kept at a constant temperature by means of a tempering medium.

The thorough mixing necessary according to the method of the invention to avoid sedimentation and increase the impact quota of the erythrocytes is obtained in that the blood sample is subjected, during the course of the measurement, to a shear movement by slowly rotating the cuvette around an axis in parallel to the light beams. Such a rotation is sufficient to produce the necessary shear movement in the blood and to exclude sedimentation of the blood during the course of the measurement. The rotation rate may be from 0.1 to 20 rpm, suitably about 2 rpm.

It has shown to be particularly advantageous if the cuvette provided for measurement is not completely filled with the blood sample so that in the course of the slow rotation of the cuvette a blood level is maintained in the cuvette and thus the cuvette walls cause, through the rotational movement, a constant stirring of the blood.

Such a method is particularly suitable for small pocket devices wherein the blood sample is for instance filled into one-way cuvettes which are thrown away after use.

Such one-way cuvettes may for instance be made from plastic material and may be provided with an opening having an elastic cover which in order to fill in the blood may be pierced by an injection needle. The air contained in the cuvette may escape either through the puncture or there may be provided a second air escape opening which is preferably closed by a gauze skin. The venting problem may also be solved in that a small rubber stopper is provided on the cuvette which expands like a bubble when filling in and absorbs the air. The air may then escape through the puncture.

Injecting with the aid of an injection needle has proved to be of a great advantage in order to obtain a thorough mixing of the blood sample. It is self-evident that in the method of the invention other mixing processes may be applied as well. In case of series measurements for instance, a motorically driven feed pump may be provided which when filling in the blood provides at the same time for the thorough mixing thereof.

In accordance with a further particularly advantageous embodiment of the method of the invention, the blood sample is subjected, during the course of the measurement, to a small-scale shear by slowly rotating a rotation body provided within the cuvette.

Such a rotation body may be of any shape and may be driven from the outside.

While the rotation rate of such a rotation body is about the same as has been stated above for the rotation of the cuvette, a thorough mixing of the blood sample by a correspondingly rapid rotation by means of such a rotation body prior to the measurement may be obtained as well. In addition to this rapid rotation, mixing of the blood sample prior to the measurement may also be effected through injection with the aid of a needle or by means of a pump aggregate.

The blood sample used in the method of the invention may be used with, or without, respectively, anticoagulants because the measuring process is normally performed very rapidly (within about 60 seconds as a rule).

It has shown to be suitable to so perform the measurement that the transmission is determined as a function of the time. As a rule, the transmission variation is determined in the course of 60 seconds and is suitably also recorded graphically by means of a recording device.

The measuring process, i.e. the registration of the transmission starts normally immediately after the termination of the injection of the blood sample into the cuvette or after switching the rotation body provided in the cuvette from the high to the low rate. After the expiration of a predetermined period of time (60 seconds as a rule), the measurement is automatically terminated.

When employing the rotation body in the cuvette, the method of the invention may very easily be fully automatized and may be used for series determination by automatizing the introduction of the blood samples, the dispersing, the measuring under shear movement, the draining of the blood samples, and the cleaning of the cuvette as well as the drying of the cuvette.

With a view to the short measuring time, the hitherto extremely time-consuming method for the determination of the blood sedimentation rate may be reduced to a very small period of time and particularly in big hospitals blood sedimentation processes may be automatized and may so to say be performed on an assembly line.

The apparatus for performing the method described above comprises according to the present invention a photometer and a cuvette containing the blood sample provided in the horizontal beam path of the photometer and is characterized in that the cuvette is rotatable around an axis provided in parallel to the light beams. Motion of the cuvette may be performed in any optional way, suitably however by means of an electromotor with a corresponding reduction gear included.

The rotation rate is within a range of from 0.1 to 20 rpm, preferably it is about 2 rpm. The distance between the two cuvette discs amounts, in accordance with the present invention, to about 0.1 to 2 millimeters, preferably to about 1 millimeter.

The cuvette used in the apparatus according to the present invention is suitably closed from all sides and is provided with at least one filling opening closed by elastic material. If the cuvette is manufactured from plastic material instead of the common glass, the filling opening may for instance be provided as a thinned location in the wall where a so-called thin-walled fish skin made of the same material as the cuvette closes this filling opening. By means of an injection needle, this fish-skin may easily be pierced and the blood sample to be tested may be filled into the cuvette while it is at the same time thoroughly mixed.

In accordance with an advantageous embodiment of the present invention, the cuvette employed in the apparatus of the invention to receive the blood sample to be tested includes a rotation body driven by a motor. Motion suitably achieved from outside of the cuvette may suitably be effected by means of a magnetic coupling through the wall material of the cuvette. To this end, the rotation body is partly ferromagnetic, it includes for instance a small soft iron bar enclosed in either glass or inert plastic material and may then, similarily to the so-called magnetic stirrers, be brought into rotation from the outside by means of a magnet driven with the corresponding speed by an electromotor rotating at the cuvette wall.

An embodiment so characterized of the present invention excells in particular advantages.

To begin with, all sealing problems are eliminated. The rotation body provided in the interior of the cuvette may be rotated with any speed from the outside. This means that the blood sample filled into the cuvette may, if necessary, be thoroughly mixed by a more rapid rotation of the rotation body while no particularly extensive measures have to be taken.

The speed of the rotation body necessary for a thorough mixing at the beginning of the measurement is between about 20 and 200 rpm, for the subsequent measurement it is within the range of about 0.1 to 20 rpm, preferably of about 2 rpm.

The rotation body is suitably provided as a flat disc and includes for the support of the shear movement of the blood sample profilings which are either elevated or constitute recesses in the rotation body. It may also be made as a fan wheel. Similar profilings may also be provided on the cuvette wall facing the rotation body by which the shear movement is substantially assisted.

A further embodiment of the apparatus of the invention includes a cuvette containing the sample arranged in the horizontal beam path of a photometer one side wall of which, which is in the beam path, is rotatable.

In accordance with a particularly advantageous embodiment of the apparatus of the invention, the rotatable side wall of the cuvette in the beam path is driven by a motor with any optional, as a rule however constant, speed.

It has in addition shown to be very advantageous if profilings are provided on the rotatable side wall of the cuvette which support the shear movement (thorough mixing) of the sample. These profilings may either be elevated or may constitute recesses. It has shown to be particularly suitable if the profilings are vane-shaped.

Also as a support of the shear movement of the sample contained in the cuvette, profilings are provided, in accordance with a further advantageous embodiment of the present invention, on the stationary cuvette wall which together with the profilings on the rotatable cuvette wall facing it support the shear movement of the sample.

These profilings provided on the stationary cuvette wall, too, may be elevated or may also constitute recesses.

In accordance with a further advantageous embodiment of the present invention, the cuvette is enclosed by a housing flooded by a tempering medium. This tempering medium which is kept, by means of a thermocouple, at a constant temperature, either below normal temperature, at normal or above normal temperature, provides that the sample in the cuvette is always at the same temperature so that in this way the temperature effect is excluded in these measurements.

Execution of the measuring method according to the invention is substantially simplified with the aid of a particularly advantageous embodiment of the apparatus of the invention wherein the cuvette includes two openings for the entrance and the drainage of the sample. These openings which are suitably provided in the stationary portion of the cuvette make possible a continuous measurement of liquids and permit also a more rapid measurement of individual samples.

By passing a cleaning medium, the cuvette is cleaned after the removal of the tested blood and is available for a refill with a further sample.

The openings are suitably provided to be closed.

On the other hand, an injection needle may directly be mounted to the openings by which the sample in question, if necessary after a corresponding tempering process of the syringe contents in a bath having a corresponding temperature, is filled into the cuvette.

The photometer serving the determination of the light transmission is suitably provided with a recorder for the registration of the light permeability of the sample as a function of the time.

On the other hand, other digital measuring devices may also be attached to the photometer by means of which the measured values may be determined and if necessary also recorded.

The apparatus of the invention makes possible with the continuous rotation of the cuvette wall a continuous examination of different blood samples and renders automatization of blood testing possible. Controlled electronically, the cuvette is filled with the sample, the result is measured and recorded, the cuvette is cleaned, dried and filled with the subsequent sample. The result may be read off digitally or may be printed out by a printer. The individual measurement may be extended at discretion as sedimentation is avoided by the shear movement caused by the rotating cuvette wall.

Based on the embodiments shown in the attached drawings, the apparatus of the invention for the measurement of the aggregation rate of the red blood corpuscles in the blood will be explained in detail. In the drawings.

Figure 1:
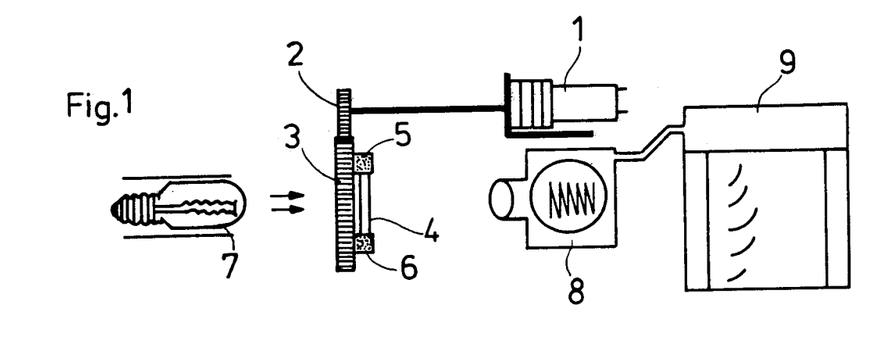
FIG. 1 is a schematic view of the apparatus of the invention including a rotatable disc cuvette.

The apparatus of the invention shown in FIG. 1 comprises a disc cuvette 4 driven by a motor 1 via a tooth wheel gear 2, 3; the cuvette is clamped with the aid of rubber stoppers 5, 6 provided on tooth wheel 3. It is arranged in the beam path of the light beams emenating from lamp 7 and impinging, behind cuvette 4, upon photocell 8. The electric signals generated thereby are recorded by recorder 9 after a corresponding amplification.

Figure 3:
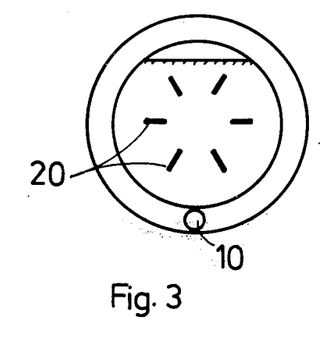
FIG. 3 is a schematic side view of a rotatable disc cuvette provided with a filling opening.

In FIG. 3 the rotatable disc cuvette is shown again in an enlarged schematic view. The degree of admission can be taken from this figure as well.

Filling is brought about through the fish skin covered filling opening 10 which may be pierced by means of a syringe.

On the opposite side of the cuvette, a second opening provided with a capillary opening may be provided through which the air contained in the cuvette may escape.

Instead of the fish skin closure which is integrally made with the cuvette, there may also be used a later-included closure of elastic material which may also be pierced by the syringe.

By this injection under pressure of the blood into the disc-shaped cuvette, a thorough mixing of the blood is reached so that immediately after the insertion of the cuvette into the beam path of lamp 7 measurement may be started, the cuvette being set into slow rotation by means of motor 1.

Figure 2:
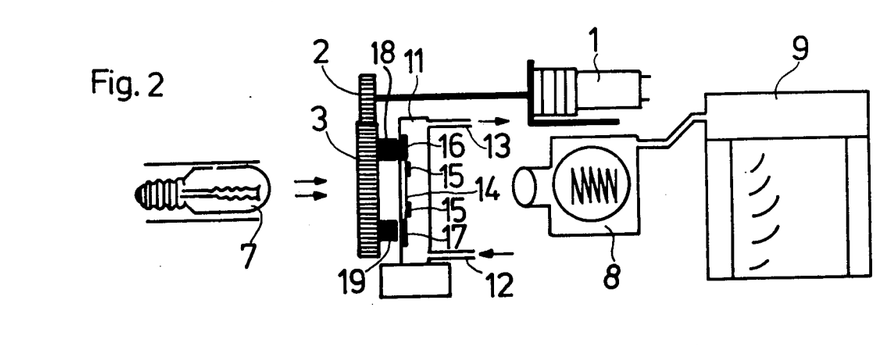
FIG. 2 is a schematic view of the apparatus of the invention including a disc cuvette incorporating a magnetically driven rotation body.

In the embodiment of the apparatus of the invention shown in FIG. 2, a disc cuvette 11 is employed which is firmly secured in the beam path of lamp 7 and is provided with a feed opening 12 and a drain opening 13. In the interior of disc cuvette 11, a rotation body 14 is provided which includes profilings 15 to support the shear movement and which includes furtheron, as a drive, ferromagnetic areas 16 and 17. On tooth wheel 3 driven by motor 1 via tooth wheel pinion 2, magnetic bodies 18 and 19 are provided which act through the cuvette upon the ferromagnetic areas of the rotation body and, if tooth wheel 3 is rotating, set it into rotation motion as well.

Motor 1 is suitably provided with two different speed ranges so that by a mere electric switch-over a high rotation speed may be adjusted in the beginning by which the blood sample introduced into the cuvette is thoroughly mixed, and subsequently, after switching down to the lower rotation speed the factual measuring process may be performed. This measuring process is performed in the same way as described in connection with FIG. 1.

Figure 4:
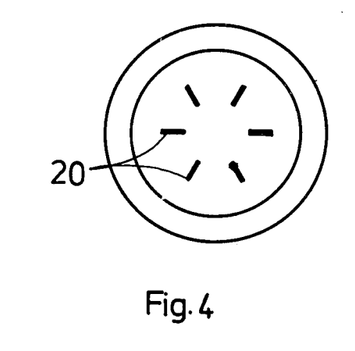
FIG. 4 is a side view of an opened rotatable disc cuvette.

In FIG. 4, a disc cuvette is shown in the opened state, that means one side wall has been taken away so that the profilings 20 provided on the rear side wall are visible.

Figure 5:
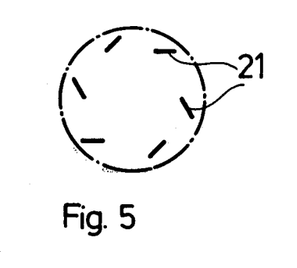
FIG. 5 is the profiled side wall of the disc cuvette of FIG. 4.

In FIG. 5, the removed side wall is shown, and the profilings 21 provided on this side wall are visible as well.

Figures 6, 8, 9:
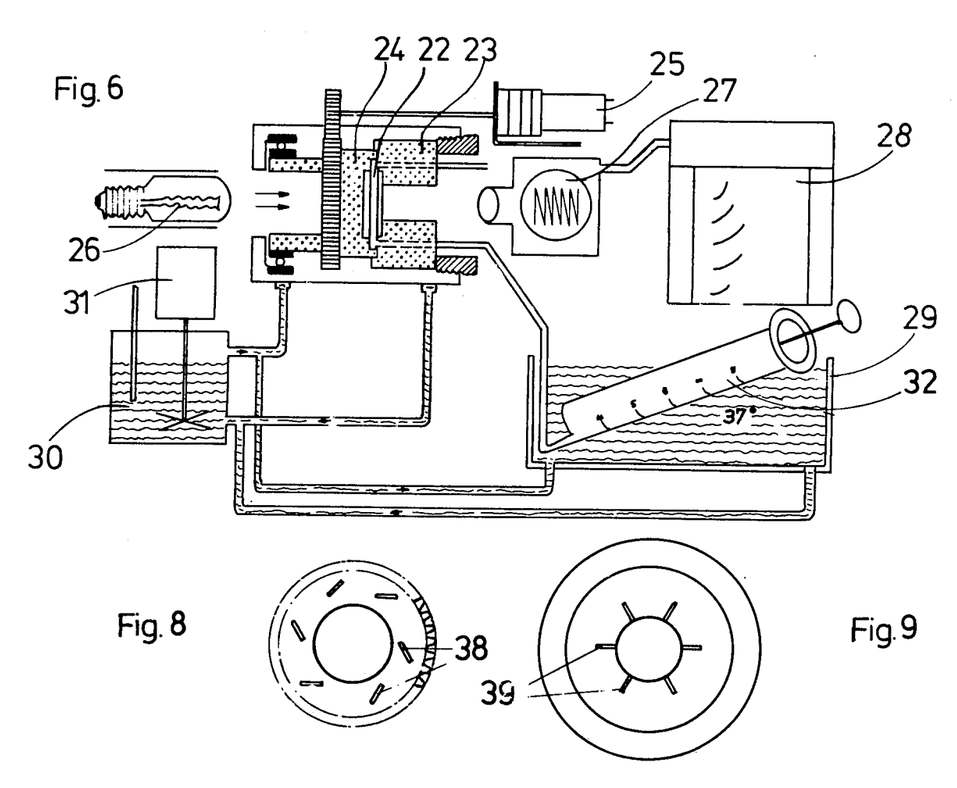
FIG. 6 is a schematic view of a further apparatus of the invention for measuring the aggregation rate of particles suspended in a liquid.
FIG. 8 is a view of the rotatable cuvette wall.
FIG. 9 is a view of the stationary cuvette.

The apparatus of the invention schematically shown in FIG. 6 comprises a cuvette including the measuring chamber 22 to receive the blood sample to be tested and including a stationarily secured cuvette portion 23 and a rotatably arranged cuvette wall 24, which may be set into rotation by a motor 25 via a tooth wheel gear and where the cuvette is set into the beam path of a photometer comprising a mercury quartz lamp 26 and a photomultiplier 27 and where the photomultiplier 27 is followed by a recorder 28. Cuvette 22 is provided with a housing for passing a tempering medium 30 which keeps the cuvette, and thus the sample to be tested, at a constant temperature. Electromotor 31 serves for stirring the tempering medium. The blood sample is injected by means of syringe 32, kept in tempering bath 29 at a temperature of 37° C., into cuvette chamber 22 and is examined with respect to the variation of the transmission as a function of time.

Figure 7:
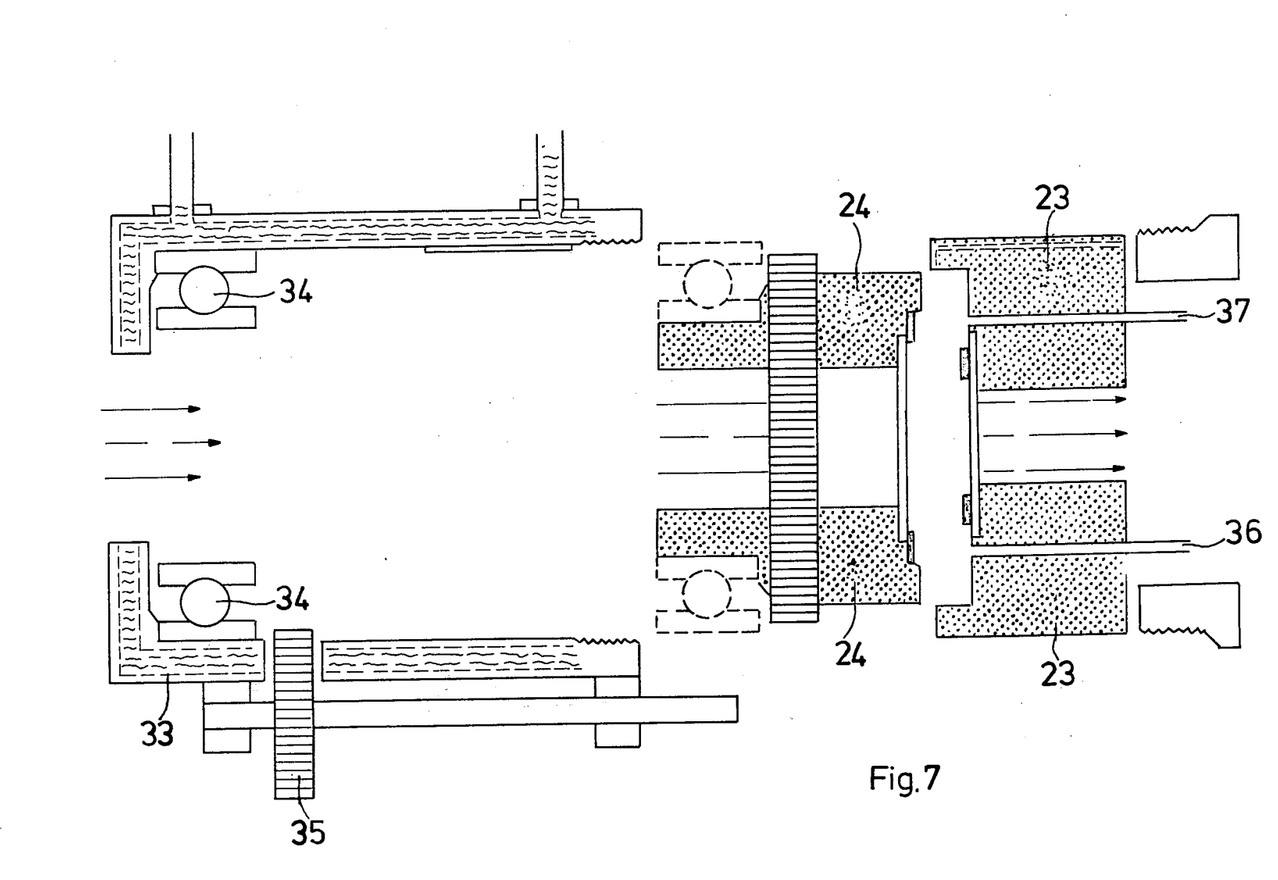
FIG. 7 is an enlarged detail of the cuvette to receive the sample.

In FIG. 7, the structure of the cuvette is again shown in detail. In housing 33 flooded by a cooling agent, the rotatable cuvette wall 24 is rotatably mounted by means of ball bearings 34 and may be set into rotation via tooth wheel gear 35.

By mounting the stationary cuvette portion 23, measuring chamber 22 is formed into which via filling and draining openings 36 and 37 the sample to be tested is introduced into measuring chamber 22.

The view of the rotatable cuvette wall shown in FIG. 8 shows the profilings 38 on it in the shape of reliefs which support the shear movements of the sample to be tested.

In FIG. 9, the shown stationary cuvette wall exhibits also profilings 39 in the shape of reliefs which cooperate with profilings 38 provided on the rotatable cuvette wall and add to the increase of the shear movement of the blood sample to be tested in the measuring cell.

The rotation rate of rotatable cuvette wall 24 is in the range of from 0 to 20 rpm and it is preferably 1 rpm.

In the determination of the aggregation rate of erythrocytes as an analogue determination relative to the determination of the blood sedimentation rate after Westergren, the measuring time usually amounts to 1 minute.

In the particular embodiment of the invention shown in FIG. 2, the relation of the drawing to reality is about 2:1.

In such an embodiment of the invention, it has shown to be suitable that the layer thickness in the cuvette between the two plane parallel glass plates is about 1 millimeter.

Figure 10:
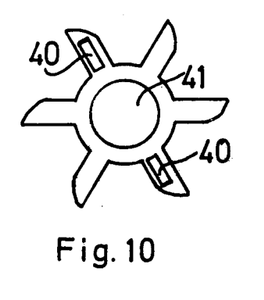
FIG. 10 is a rotation body provided as a fan wheel.

The rotation body of FIG. 10 shaped as a fan wheel includes on two blades facing each other one ferromagnetic body 40 each which cooperate with the magnetic field rotating outside and cause the rotation of the rotation body within the cuvette. The somewhat inclined blades produce the shear movement in the blood sample during the measurement which is caused through the centric opening 41 of the rotation body.

It is apparent from the particular arrangement of the profilings on the disc-shaped cuvette illustrated in FIGS. 3–5, 8 and 9 that the shear movement of the blood sample takes place around an axis that is substantially parallel to the path of the light beam which impinges on the cuvette. The rotatable body produces a similar shear movement. As is also apparent, the axis of rotation of the cuvette (in those embodiments where the cuvette is rotated) and the axis of rotation of the rotatable body (in those embodiments wherein the rotatable body is utilized) is preferably substantially coincident with the path of the light beam.

We claim:

1. A method for measuring the rate of aggregation of particles suspended in a liquid and in particular for measuring the rate of aggregation of red blood corpuscles in the blood, comprising the steps of:
   introducing a blood sample into the interior of a disc-shaped cuvette having opposed side walls, the latter being disposed in the path of a light beam of a light source;
   subjecting the blood sample contained within said cuvette to a shear movement around an axis of shear movement to prevent substantial sedimentation of the formed aggregates, said shear movement axis being substantially parallel and substantially coincident to said light beam path; and
   measuring the change in intensity of the light beam which impinges on the blood sample within said cuvette.

2. A method according to claim 1 wherein said blood sample is subjected to a shear movement by rotating said cuvette about an axis of rotation, said axis of rotation substantially coinciding with said light beam path.

3. A method according to claim 1, wherein said blood sample is thoroughly mixed upon being introduced into said disc-shaped cuvette.

4. A method according to claim 1, wherein the intensity variation of said light beam passing through through said blood sample is measured.

5. A method according to claim 1, wherein the intensity variation of said light beam reflected from said blood sample is measured.

6. A method according to claim 2, wherein said cuvette is only partially filled with said blood sample for the measurement.

7. A method according to claim 1, wherein said sample is subjected to said shear movement by rotating a side wall of said cuvette.

8. A method according to claim 1 wherein said blood sample is subjected to said shear movement by rotating the opposed side walls of said cuvette.

9. A method according to claim 1 wherein said blood sample is subjected to said shear movement by rotating a body provided within said cuvette.

10. A method according to claim 1 wherein said blood sample is introduced into the interior of said cuvette by injecting the same under pressure into said cuvette thereby completely dispersing the blood corpuscles.

11. A method according to claim 1 wherein said sample is kept, during the measurement, at a constant temperature by means of a tempering medium.

12. Apparatus for measuring the rate of aggregation of particles suspended in a liquid and in particular for measuring the rate of aggregation of red blood corpuscles in the blood, comprising:
   light source means for projecting a light beam along a light beam path;
   a disc-shaped cuvette having opposed side walls adapted to contain a blood sample, said cuvette being mounted in said light beam path for rotation about an axis of rotation which substantially concides with said light beam path;
   means provided within said cuvette for subjecting the blood sample to a shear movement around an axis of shear movement upon rotation of said cuvette, said shear movement axis being substantially parallel to said light beam path; and
   means for measuring the change in intensity of the light beam which impinges on the blood sample within said cuvette.

13. Apparatus as recited in claim 12 wherein said cuvette has a rotatable side wall and an opposed stationary side wall and wherein only said rotatable side wall is rotated to effect said shear movement.

14. An apparatus according to claim 12, wherein said cuvette is rotated by an electromotor with a speed of from about 0.1 to about 20 rpm.

15. An apparatus according to claim 12, wherein the rotation rate of said cuvette is about 2 rpm.

16. An apparatus according to claim 12 wherein said cuvette is closed from all sides and is provided with at least one filling opening closed by elastic material.

17. An apparatus according to claim 13, wherein said rotatable side wall of said cuvette in said beam path is driven by a motor with a constant speed.

18. An apparatus according to claim 13 wherein on said rotatable side wall of said cuvette profilings are provided to effect the shear movement of said sample.

19. An apparatus according to claim 18, wherein on the stationary cuvette wall profilings are provided effecting together with said profilings on said opposed rotatable cuvette wall the shear movement of said sample.

20. An apparatus for measuring the rate of aggregation of particles suspended in a liquid and in particular for measuring the rate of aggregation of red blood corpuscles in the blood, comprising:
light source means for projecting a light beam along a light beam path;
a disc-shaped cuvette mounted in said light beam path having opposed side walls adapted to contain a blood sample;
a rotatable body disposed within said cuvette adapted to rotate in the plane of said cuvette around an axis substantially parallel to said light beam path to subject the blood sample to a shear movement upon rotation of said body;
magnetic means located outside of said cuvette for magnetically coupling to and rotating said rotable body; and
means for measuring the change in intensity of the light beam which impinges on the blood sample within said cuvette.

21. An apparatus according to claim 20 wherein said rotatable body in order to effect the shear movement of said blood sample is provided with profilings.

22. An apparatus according to claim 20 wherein the rotation rate of said rotatable body is from about 0.1 to about 20 rpm.

23. An apparatus according to claim 22, wherein the rotation rate of said rotatable body is about 2 rpm.

24. An apparatus according to claim 20 wherein said rotatable body is driven with a rapid and with a slow rotation rate.

25. An apparatus according to claim 20 wherein said cuvette is surrounded by a housing flooded by a tempering medium.

26. An apparatus according to claim 20 wherein said cuvette is provided with two openings for the entrance and the drainage of said sample.

27. An apparatus according to claim 26, wherein said openings are closable.

28. An apparatus according to claim 20 further including a recorder for recording the light permeability of said sample as a function of the time, said recorder being connected to said photometer.

29. An apparatus according to claim 20 wherein said photometer is connected to a digital indicator.

30. An apparatus according to claim 12 wherein the distance between said cuvette side walls is from about 0.1 to about 2 millimeters.

31. An apparatus according to claim 30, wherein the distance between said cuvette side walls is about 1 millimeter.

32. A method for the automatic measurement of the aggregation rate of particles suspended in a liquid according to claim 1 wherein said blood sample to be tested is fed into said cuvette, the measurement is made, the sample is washed out by means of a cleaning agent, the cuvette is dried by means of a gas passed through it and is fed again with a new sample.

* * * * *